United States Patent [19]

Tumas

[11] Patent Number: 5,682,617
[45] Date of Patent: Nov. 4, 1997

[54] LATEX STOCKING BANDAGE

[75] Inventor: Alfredo Tumas, 37 Lincoln Ter., Yonkers, N.Y. 10701-1905

[73] Assignee: Alfredo Tumas, Yonkers, N.Y.

[21] Appl. No.: 677,622

[22] Filed: Jul. 8, 1996

[51] Int. Cl.[6] .............................. A41B 11/00; A61F 13/08
[52] U.S. Cl. .................. 2/239; 2/242; 602/63; 602/65; 604/293
[58] Field of Search ........................... 2/239, 61, 22, 2/168, 240, 241, 242; 36/2 R, 7.1 R, 7.4, 7.3, 8.1, 4, 10; 602/23, 27, 62, 63, 65, 66, 61, 75, 77; 604/293

[56] References Cited

U.S. PATENT DOCUMENTS

| | | | |
|---|---|---|---|
| 99,412 | 2/1870 | Curtis | 2/239 |
| 707,659 | 8/1902 | Ware et al. | 2/239 |
| 1,544,641 | 7/1925 | Guinzburg | 2/61 |
| 1,708,810 | 4/1929 | Vrabek | 2/242 |
| 1,785,033 | 12/1930 | Lorenz et al. | 2/242 |
| 2,015,648 | 9/1935 | Gammeter | 18/41 |
| 2,033,626 | 3/1936 | Gammeter | 2/242 |
| 2,244,871 | 6/1941 | Guinzburg | 2/22 |
| 2,601,851 | 7/1952 | Jones | 604/293 |
| 3,384,083 | 5/1968 | Cozza et al. | 604/293 |
| 3,550,594 | 12/1970 | Upton, Jr. | 604/293 |
| 4,069,600 | 1/1978 | Wise | 2/239 |
| 4,622,035 | 11/1986 | Palmer et al. | 604/293 |
| 5,614,202 | 3/1997 | DeFina | 424/402 |

FOREIGN PATENT DOCUMENTS

| | | | |
|---|---|---|---|
| 261676 | 5/1963 | Australia | 604/293 |
| 417187 | 1/1934 | United Kingdom | 604/293 |

*Primary Examiner*—Amy B. Vanatta

[57] ABSTRACT

A sock of soft elastic latex material from 0.003 to 0.005 inches in thickness and with a modulus of elasticity of from 450 to 500. It is non-porous and non-permeable and it is used to maintain creams, treatment lotions and moisturizing agents in contact with the skin surface of lower limbs. It is also useful in the prevention of hypothermia.

4 Claims, 2 Drawing Sheets

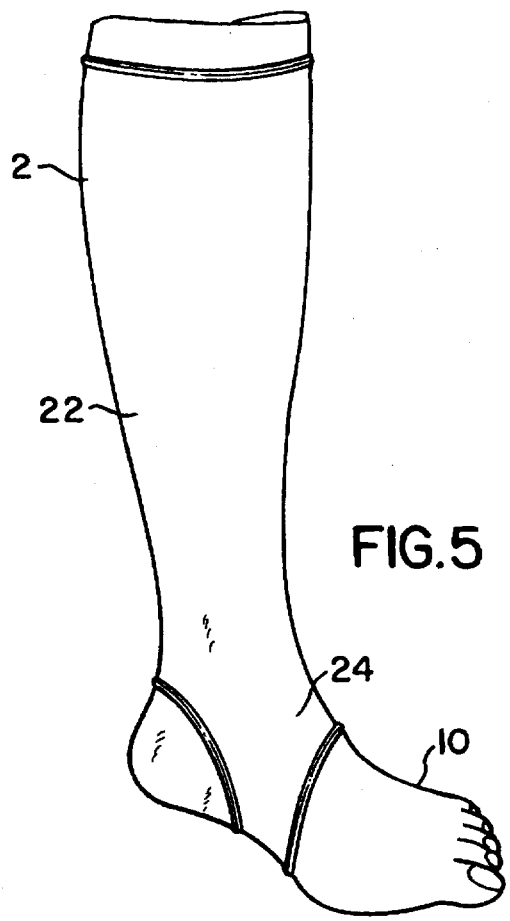
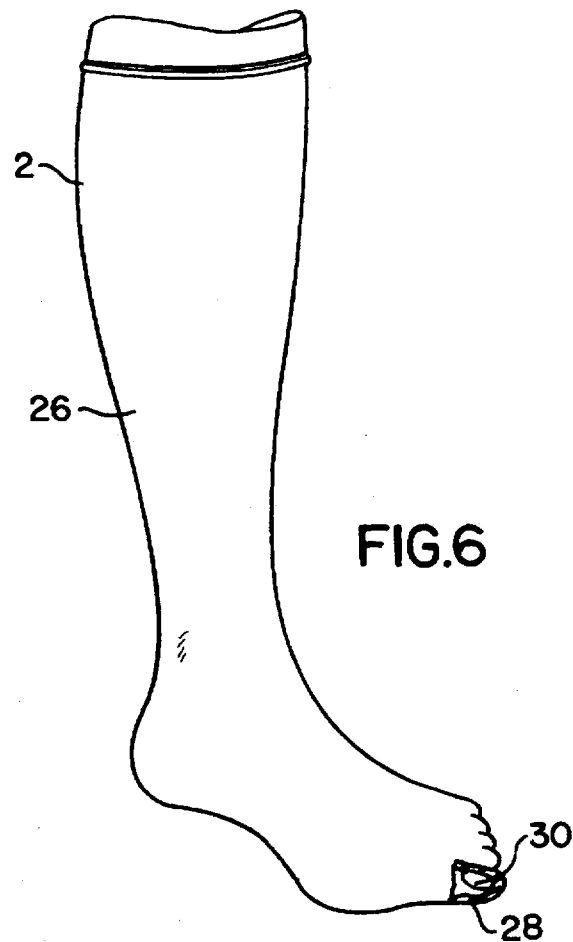
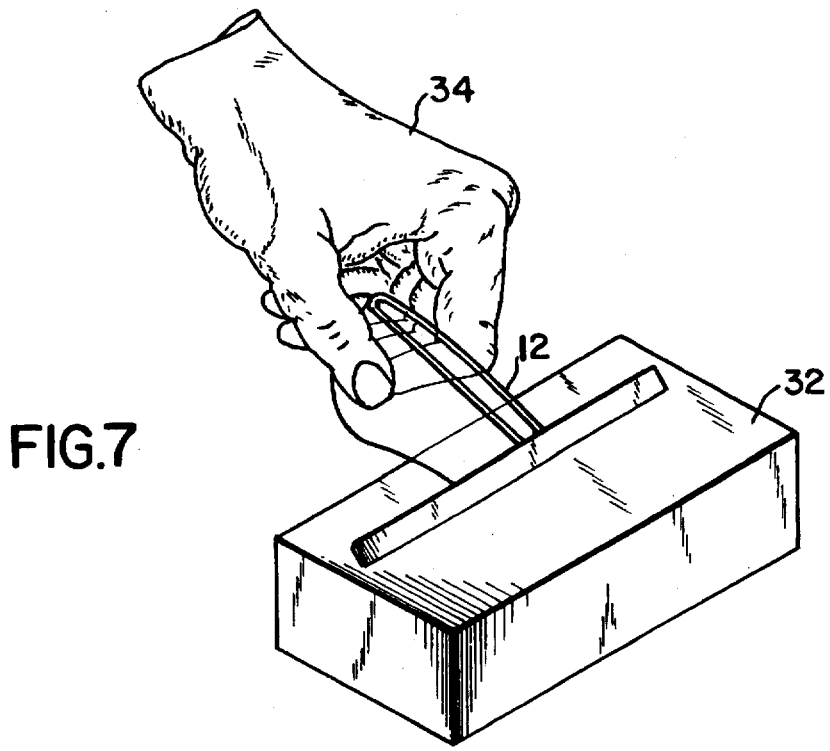

LATEX STOCKING BANDAGE

BACKGROUND OF THE INVENTION

1. Field of the Invention

This invention relates to medical stockings and in particular to a special stocking for treating various problems on the legs such as fluid retention of the legs and feet, poor circulation, diabetes, allergies, skin problems, and psoriasis. The sock of the present invention besides lending support is particularly adapted to holding creams, ointment, lotions and other medicaments such as moisturizing agents in contact with the skin surface of the lower extremities.

2. Prior Art

Applicant is not aware of any prior art which discloses directly or indirectly or suggests a special sock such as applicant has discovered.

U.S. Pat. No. 4,069,600—WISE discloses an athletic foot protector comprising a porous elastic sock which is utilized in a size one smaller than the foot to which it is applied so that it will stretch in all directions to assure that there is no motion between the foot and the elastic sock. This provides a protective covering against abrasion. The sock holds the flesh on the foot away from it, but the porous elastic materials allow perspiration to pass through it. The elastic covering is used in conjunction with an absorbent material such as a knit sock to conduct perspiration away from the elastic covering.

U.S. Pat. No. 4,204,345—BRADLEY discloses a plastic sock for use in combination of a boot to facilitate insertion of the foot in the boot and to keep the feet dry. It comprises an adjustable tubular sock in combination with the boot with a liquid impermeable single sheet of tubular configuration. It is in the form of a unitary sock-like structure, but is air permeable and it is usually made of polypropylene or urethane film, but it is liquid impermeable. The purpose is to maintain the feet dry while wearing boots and to facilitate insertion of the foot into an adjustable boot.

U.S. Pat. No. 4,295,022—STOCKLI et al discloses a boot for aquatic activities comprised of elastomeric material covered by nylon on one or both sides, together with an outersole of materials such as non-cellular rubber which is directly vulcanized to the end. The boot is long-lasting and is designed particularly for underwater diving usage.

Other patents of background interest only are: U.S. Pat. No. 4,748,749—COLVARD, U.S. Pat. No. 4,809,447—PACANOWSKY et al, U.S. Pat. No. 4,845,862—PHILLIPS, Jr. et al, U.S. Pat. No. 5,339,545—PARIS, U.S. Pat. No. 5,402,540—WILLIAMS, U.S. Pat. No. 5,483,703—WILLIAMS, U.S. Pat. No. 5,430,896—BISLEY.

The prior art developed by Applicant's preliminary search does not show the use of a sock such as the present case. There are protective rubber socks which are usually in combination with boot materials or other plies of fabric. The elastomer is water permeable or at least water vapor permeable as opposed to the stocking of the present application which is neither liquid nor vapor permeable.

SUMMARY OF THE INVENTION

This invention comprises a sock or a knee-high bootie or leg warmer constructed of soft latex material such as the type used in construction of surgical gloves. It is very thin but is moisture or vapor impermeable. It is particularly useful to maintain creams, ointments, lotions, and moisturizing agents in direct contact with the skin surface of the lower limbs. It is useful for fluid retention on the legs, arms, and feet due for poor circulation, diabetes, allergies, and various skin problems such as psoriasis.

The sock is made of very soft waterproof latex which also can serve as an insulator to conserve body heat preventing rapid lose of body heat when exposed to the cold elements. It is thus useful in the prevention of hyperthermia caused by exposure to severe cold weather conditions. Preferably, the product is made of material similar to that used in soft surgical latex gloves and is designed to be soft, disposable, inexpensive and non-sterile. It can be available at a very reasonable price.

The sock of the present invention is particularly useful in the application of medicated creams, ointments, lotions, and moisturizing agents to hold them in contact with the skin surface of the legs and feet. It is very effective and promotes healing faster than by simply the application of creams and the like to the skin surface in the usual manner in which they are quickly worn away when there is no protective covering for them.

Where psoriasis and other conditions are widespread over the lower extremities it is generally impractical to apply a conventional bandage material to isolate the medicated surfaces from clothing or from contact with other persons or surfaces. Up to the time of the present invention there has been no other type of waterproof sock that could be worn as an insulator to prevent hypothermia and also which was thin enough, waterproof, and vapor-proof so that it could serve as an easily applied protection to feet and legs.

In the preferred embodiment, the toe area is in effect stubbier and it is easily fitted to a perfect fit because of the softness and elasticity. It is a very comfortable and produces a comforting feeling when worn. There is no movement of the sock up or down or about on your leg because of the elastic energy holding it in place.

In the application of medicaments the sock of the present invention serves to take some of the strain off of the ankles. Because of the unique design, particularly of the toe area, there is almost a guarantee of a perfect fit because of the softness and elasticity. One experiences a comfortable feeling and no slipping or travelling up or down the feet by the sock when applied to the extremities. The sock which serves as a foot or leg warmer fits everyone perfectly because of the desired amount of elasticity. It is non-binding and non-irritating and offers great support which increases comfort and circulation. It is particularly useful in the cases of poor circulation, diabetes, allergies, limitation on swelling and fluid retention just to name a few of the many useful applications for the bootie sock of the present invention. It is particularly useful for the application of moisturizers and creams applied to peeling, drying, and/or cracked skin. Because of the moisturizing effect, the feet feel soft and a minimization of repulsive odors is accomplished as well.

While the socks are made in a variety of ways, they are in texture similar to surgical latex gloves, very soft and disposable, waterproof and inexpensive. While they may be sterile, they need not be.

BRIEF DESCRIPTION OF THE DRAWING

Referring to the accompanying drawing that forms part of this application

FIG. 5 is a perspective view of the lower portion of the leg and foot showing a full length sock with the heel and toe portions exposed;

FIG. 6 is a full length sock covering the entire foot and with a portion broken away to show the latex material covering the foot;

FIG. 7 is a perspective view showing how the articles of the present invention may be dispensed from a package similar to a tissue dispenser.

ILLUSTRATIVE SPECIFIC EMBODIMENTS

Figure 1:
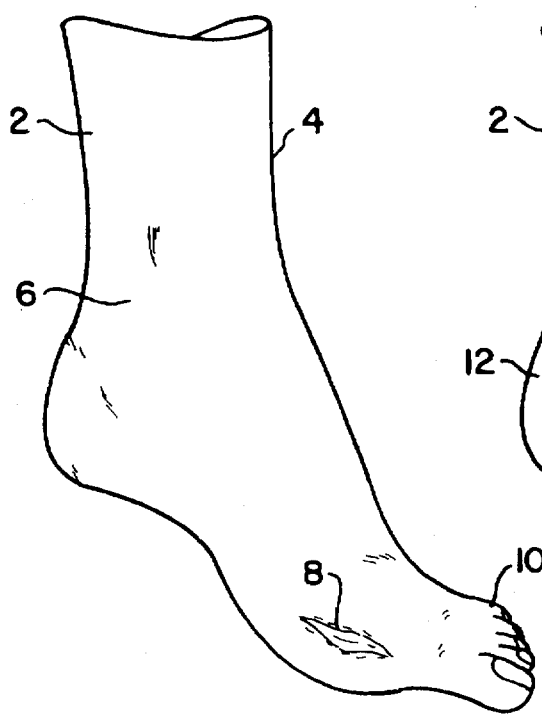
FIG. 1 is perspective view of an individual's foot showing a lesion rearwardly of a large toe.

Preferred illustrative embodiments of the present invention are shown in the accompanying drawing comprise a sock or bootie shape shown in the figures.

It is enclosed from the toes to the upper calf and it is made of nonporous nonpermeable stretchable latex sheet material. The latex is of the type that is used in surgical gloves and available under the trademark Durotex Aladan Corporation.

The material is generally from 0.003 to 0.005 inches in thickness and it has a modulus of elasticity of 450–500. In the preferred embodiment the foot portion is totally enclosed and mock pockets or retention areas are molded into the fore portion of the areas to individually retain each toe of the wearer.

In preferred embodiments the socks come up full length to the knee joint, however, intermediate lengths are envisioned within the scope of the application also. It is generally preferred that the toe area be enclosed, however, the leg liner or stocking may also be of the other shapes shown in the drawing.

The stockings of the present invention as indicated are elastic latex and will fit snuggly over the skin surfaces of the portions of the leg or foot that are covered, keeping moisture and medicaments in close contact with the skin and preventing evaporation or loss by rubbing on clothing or other objects. They are highly effective in providing covering for medicaments such as creams and pastes that may be prescribed for the particular condition of the individual and they serve to keep dirt and other foreign matter away from the area being treated.

Turning to the attached drawings:

FIG. 1 shows a portion of a person's leg and shin 4, ankle 6 to area 10 and sore to be treated according to the present invention.

Figure 2:
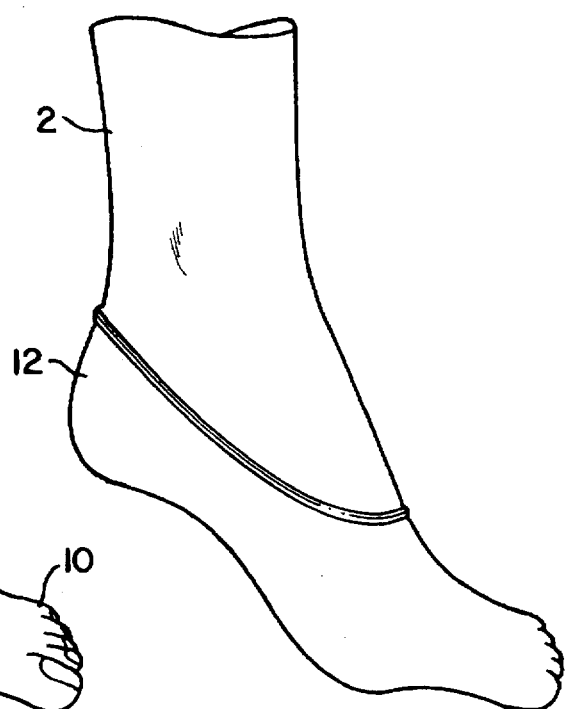
FIG. 2 is a similar perspective view of the same foot showing the lower portions of the foot covered with an elastic-stretch latex sock according to the present invention.

FIG. 2 shows a leg with a plastic low cut sock 12 covering the foot portion of the patient.

Figure 3:
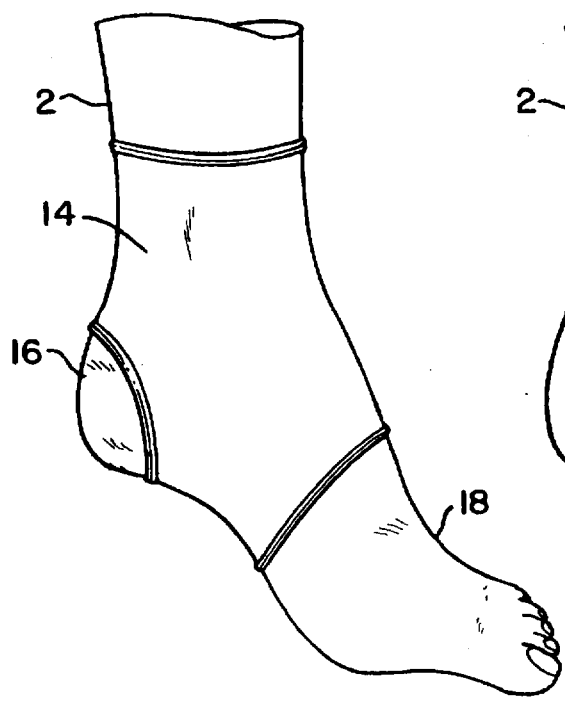
FIG. 3 is a similar perspective view showing the ankle portion and the instep portion of the foot covered with a cover according to the present invention with the toe portions and the heel portions of the foot free of the covering.
Figure 4:
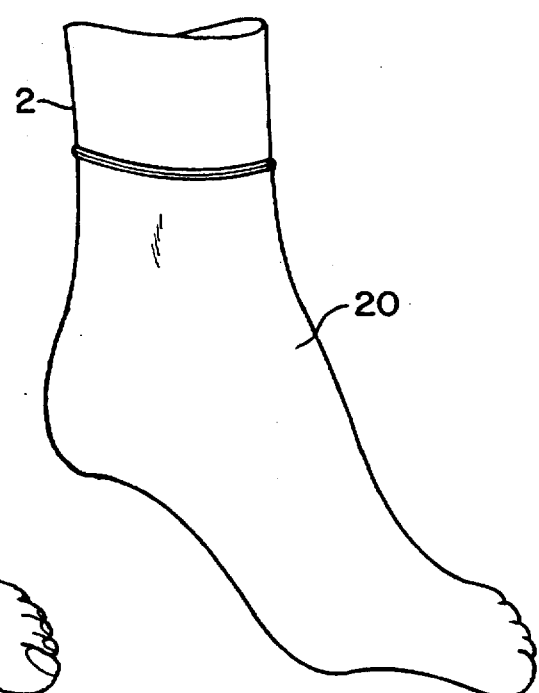
FIG. 4 is a similar perspective view the foot cover with an anklet size sock of latex in accordance with the present invention.

FIG. 3 a further variation is shown with an ankle-type of sock 14 with the heel 16 and toe and forward portion of the foot 18 uncovered. An anklet sock 20 is shown in FIG. 4 and a full length stocking in FIG. 5, secured above the instep, with the heel and toe area exposed.

FIG. 6 full length stocking 26 is illustrated with a cut away portion shown at 28, large toe at 30.

FIG. 7 a mini-sock 12 is shown being pulled from a dispensing box 32 with a hand of an individual indicated at 34.

While the invention has been described by reference to an illustrative embodiment, it is not intended that the novel device be limited thereby, but that modifications thereof are intended to be included as falling within the broad spirit and scope of the foregoing disclosure, the following claims and the appended drawings.

What is claimed is:

1. A non-porous lightweight non-permeable stretchable elastic latex stocking for use in treating skin irritations of the leg by the application of treatment lotions to the affected skin area of the leg, said stocking serving to hold said lotion in contact with the irritated areas of said leg due to its elasticity, said elastic latex stocking having a thickness of from 0.003 to 0.005 inches and a modulus of elasticity of from 450 to 500.

2. A stocking as claimed in claim 1 that is ankle length.

3. A stocking as claimed in claim 1 that covers the calf portion of a wearer.

4. A stocking as claimed in claim 1 covering the ankle and the lower leg portion of a wearer having an opening in the heel area and terminating in the area of a wearer's instep.

* * * * *